(12) United States Patent
Ranta et al.

(10) Patent No.: US 9,182,064 B2
(45) Date of Patent: Nov. 10, 2015

(54) CONNECTOR STRUCTURE AND A CONNECTOR STRUCTURE OF A SAMPLING TUBE OF A PATIENT RESPIRATORY TUBING

(75) Inventors: Janne Vesa-Matti Ranta, Espoo (FI); Timo Olavi Holopainen, Helsinki (FI); Juha Matti Viitala, Vantaa (FI); Jukka Antti Petteri Hakanen, Espoo (FI)

(73) Assignee: CAREFUSION CORPORATION, San Diego, CA (US)

( * ) Notice: Subject to any disclaimer, the term of this patent is extended or adjusted under 35 U.S.C. 154(b) by 0 days.

(21) Appl. No.: 13/346,764

(22) Filed: Jan. 10, 2012

(65) Prior Publication Data

US 2013/0175796 A1 Jul. 11, 2013

(51) Int. Cl.
*F16L 37/00* (2006.01)
*F16L 37/086* (2006.01)
*F16L 37/26* (2006.01)
*A61M 39/10* (2006.01)

(52) U.S. Cl.
CPC ............. *F16L 37/086* (2013.01); *A61M 39/10* (2013.01); *F16L 37/26* (2013.01); *A61M 39/1011* (2013.01); *A61M 2039/1094* (2013.01); *F16L 2201/10* (2013.01)

(58) Field of Classification Search
CPC ............ A61M 39/10; A61M 39/1011; A61M 2039/1094; F16L 37/086; F16L 37/26; F16L 2201/10
USPC .......................... 285/305, 189, 194, 326, 325; 128/202.27; 604/533
See application file for complete search history.

(56) References Cited

U.S. PATENT DOCUMENTS

| 210,923 | A | * | 12/1878 | Davies | 285/325 |
| 936,886 | A | * | 10/1909 | Hannold | 285/90 |
| 1,175,440 | A | * | 3/1916 | Hagen | 285/325 |
| 1,474,155 | A | * | 11/1923 | Krause | 285/283 |
| 2,056,562 | A | * | 10/1936 | Bridge | 285/325 |
| 2,195,013 | A | * | 3/1940 | Rastetter et al. | 285/325 |
| 4,037,654 | A | * | 7/1977 | Lien | 285/325 |

(Continued)

FOREIGN PATENT DOCUMENTS

WO 2008146181 A1 12/2008
WO WO-2010079396 A1 7/2010

OTHER PUBLICATIONS

EP Search Report issued on 2011-06-214 in connection with EP Application Serial No. 1150089.8 filed on Jan. 4, 2011.

(Continued)

*Primary Examiner* — David E Bochna
(74) *Attorney, Agent, or Firm* — McDermott Will & Emery LLP

(57) ABSTRACT

A connector structure for a fluid tube is provided. The connector structure comprises: a first connector body connected to a fluid tube; a second connector body, the first connector body and the second connector body being connectable to each other and comprising mating surfaces to create a fluid tight seal between the first connector body and the second connector body, wherein the mating surfaces comprise only vertical and/or oblique parts and are configured to press tightly against each other and form a fluid tight seal with the locking mechanism; and a locking mechanism, wherein the first and the second connector body are configured to detach from each other when the locking mechanism is not used.

19 Claims, 3 Drawing Sheets

(56) References Cited

U.S. PATENT DOCUMENTS

| | | | |
|---|---|---|---|
| 4,422,472 A * | 12/1983 | Klein | 285/326 |
| 5,829,794 A * | 11/1998 | Schulz-Hausmann et al. | 285/194 |
| 5,937,858 A | 8/1999 | Connell | |
| 5,980,506 A * | 11/1999 | Mathiasen | 604/533 |
| 6,039,043 A * | 3/2000 | Graber et al. | 128/202.27 |
| 6,059,325 A * | 5/2000 | Heckele et al. | 285/325 |
| 6,073,626 A * | 6/2000 | Riffe | 128/202.27 |
| 6,279,573 B1 * | 8/2001 | Johnson et al. | 128/202.27 |
| 6,423,053 B1 * | 7/2002 | Lee | 604/533 |
| 6,588,426 B2 * | 7/2003 | Linderoth | 128/202.27 |
| 6,668,825 B2 * | 12/2003 | Cardon | 128/202.27 |
| 6,969,357 B1 * | 11/2005 | Colman et al. | 600/529 |
| 7,185,652 B2 * | 3/2007 | Gunaratnam et al. | 128/202.27 |
| 7,188,869 B2 * | 3/2007 | Garraffa | 128/202.27 |
| 7,278,423 B2 * | 10/2007 | Serowski et al. | 128/202.27 |
| 7,325,839 B2 * | 2/2008 | Slentz | 285/189 |
| 7,721,738 B2 * | 5/2010 | Svendsen | 128/202.27 |
| 7,793,990 B2 * | 9/2010 | Robert | 285/325 |
| 8,028,692 B2 * | 10/2011 | Ho | 128/202.27 |
| 8,056,933 B2 * | 11/2011 | Liptak | 285/189 |
| 2007/0068531 A1 | 3/2007 | Matlock et al. | |
| 2008/0264413 A1 | 10/2008 | Doherty et al. | |
| 2009/0320841 A1 * | 12/2009 | Haveri | 128/204.18 |
| 2010/0136501 A1 | 6/2010 | Schuetz | |

OTHER PUBLICATIONS

European Office Action for Application No. 11150089.8, dated Jul. 29, 2015, 4 pages.

\* cited by examiner

CONNECTOR STRUCTURE AND A CONNECTOR STRUCTURE OF A SAMPLING TUBE OF A PATIENT RESPIRATORY TUBING

BACKGROUND OF THE INVENTION

1. Field of the Invention

The disclosure relates to a connector structure for a fluid tube the connector structure comprising a first connector body connected to a fluid tube, and a second connector body, the first connector body and the second connector body being adapted to be connected to each other and provided with mating surfaces to create a fluid tight seal between the first connector body and the second connector body. The disclosure relates further to a connector structure of a patient respiratory tubing.

As described above the disclosure relates to the connector structure for a fluid tube. More specifically the disclosure relates generally to a fluid connection for reducing the risk of incomplete connections resulting in leakages of fluid said connection. The disclosure relates also to sample tubing connections used in analyzing equipment such as gas analyzing equipment for patient respiratory gas.

2. Description of Related Art

In anesthesia or in intensive care, the condition of a patient is often monitored e.g. by analyzing the air exhaled by the patient for its carbon dioxide content. For this reason a small portion of the respiratory gas is delivered to a gas analyzer. The sample is carried along a sampling tube connected in one end often to a respiratory tube adapter and the other end to the gas analyzer. This sampling tube is typically disposable and must have some kind of reliable and tight connectors. Almost all pneumatic connectors in the respiratory system have tapered conical contact surfaces. Such connectors are simple, relatively easy to connect and cheap to make. The connection such as a well-known fitting called Luer-Lok, a registered trademark of Becton Dickinson of Franklin Lakes, N.J. USA, has been in general use for gas sampling but also other similar connectors with differing dimensions can be used. When used with carefully following the instructions for use they provide an airtight and reliable connection.

A gas analyzer designed to measure respiratory gas in real time provides critical data that care givers use to assess the clinical status of the patient as well as the proper functioning of the devices and the clinical set up in use. The technology used in clinical gas measurement is developing in a direction where the monitoring system is equipped with algorithms that provide caregivers proposals to readjust the clinical parameters based on the gas data. Therefore, it is of paramount importance that the data provided by the gas analyzer is correct and gives accurate and true information about the gas concentrations and their changes in the clinical set up.

Unfortunately, the connector designs used in gas sampling applications, including the widely used Luer connector, leave room for erroneous situations that can degrade the gas sample and lead to wrong clinical assessments. Specifically, it is possible to make a connection where the interfacing parts are mounted deep enough into each other so that they would not fall off from each other even though still not being secured together. Often times such an incomplete and unsecured connection is not airtight even though the gas sampling line hanging in gas detector gives a care giver the false visual impression that a proper connection has been established.

Since the analyzer creates an under pressure into the gas sample line a leak in the connection will result in ambient air diluting the gas sample going into the analyzer meaning that the air analyzed in the gas sensor no longer represents the real clinical conditions. This can lead to wrong diagnoses about the patient's clinical condition as well as wrong conclusions about the functioning of the equipment and their accessories. Specifically, patient safety may be worsened because incorrect gas data may lead to hypoxia or over dosage of anesthetic agent.

BRIEF SUMMARY OF THE INVENTION

The above-mentioned shortcomings, disadvantages and problems herein which will be understood by reading and understanding the following specification.

In an embodiment, a connector structure for a fluid tube is provided. The connector structure comprises: a first connector body connected to a fluid tube; a second connector body, the first connector body and the second connector body being connectable to each other and comprising mating surfaces to create a fluid tight seal between the first connector body and the second connector body, wherein the mating surfaces comprise only vertical and/or oblique parts and are configured to press tightly against each other and form a fluid tight seal with the locking mechanism; and a locking mechanism, wherein the first and the second connector body are configured to detach from each other when the locking mechanism is not used.

In another embodiment, a connector structure of a sampling tube of a patient respiratory gas tubing is provided. The connector structure comprising: a first connector body connected to a fluid tube; a second connector body, the first connector body and the second connector body being connectable to each other and comprising mating surfaces to create a fluid tight seal between the first connector body and the second connector body, wherein the mating surfaces comprise only vertical and/or oblique parts and are configured to press tightly against each other and form a fluid tight seal with the locking mechanism; and a locking mechanism, wherein the first and the second connector body are configured to detach from each other when the locking mechanism is not used.

In a still another embodiment at least one end of the sample tube is provided with the second connector body of the connection structure.

BRIEF DESCRIPTION OF THE DRAWINGS

The accompanying drawings, which are incorporated in and constitute a part of the specification, illustrate one or more embodiments and, together with the description, explain these embodiments. In the drawings.

DETAILED DESCRIPTION OF THE INVENTION

Figure 1:
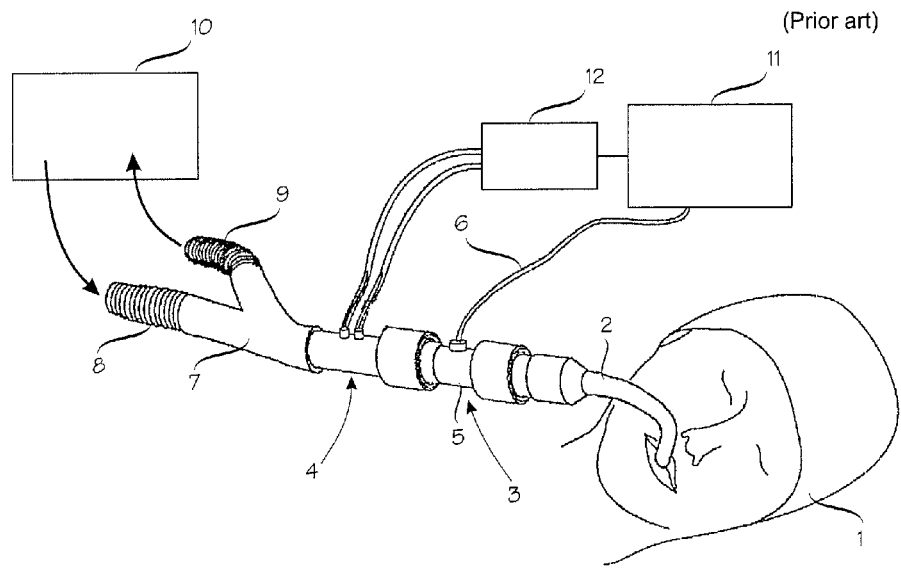
FIG. 1 shows a perspective view of an embodiment of the present invention in an operating patient care environment.

FIG. 1 shows a normal operating patient care environment. In the arrangement shown in FIG. 1 reference number 1 shows a patient and reference number 2 shows an intubation tube. Reference number 3 shows generally a patient breathing tubing. The patient breathing tubing comprises a flow sensor 4 and a connecting piece 5. The connecting piece 5 is provided with a sampling tube 6 for the analysis of gas, e.g. measurement of its concentration, which is connected between the intubation tube and an Y-piece 7 connecting the inlet hose 8 and the outlet hoses 9 of an apparatus 10 maintaining respiration.

The gas sampling tube 6 is connected to an analyzer 11, in which the gas is measured and the signal is processed so as to produce a display (not shown) showing the variations in the gas concentration under measurement as a function of time, i.e. the respiration curve or concentration readings during exhalation and inhalation.

In the arrangement of FIG. 1 the flow sensor 4 is also connected via measuring apparatus 12 to the analyzer 11, in which the signal is processed so as to produce a display (not shown) of the flow and pressure readings for inhalation and exhalation and possible other quantities derived from them. The measuring apparatus 12 may also be placed in the analyzer 11 and the gas concentration can be performed in the connecting piece 5 or as integrated with the flow sensor 4, if the device is a so-called mainstream gas sensor.

When the gas sampling tube 6 is connected to the analyzer 11 in the prior art it is quite possible that there may exist disadvantages, i.e. eventual leaks etc. discussed earlier in the text.

Figure 2:
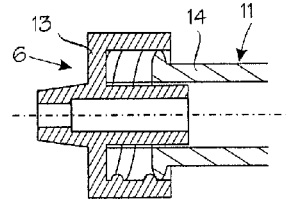
FIG. 2 shows a typical example of a prior art connector structure.

FIG. 2 shows a typical example of a prior art connector structure. FIG. 2 uses corresponding reference numbers as used in FIG. 1. FIG. 2 shows a connector using mating tapered conical contact surfaces. This prior art has been discussed earlier in the text.

The matters described above are quite familiar to a person skilled in the art and therefore said matters are not discussed here in detail.

Figure 3:
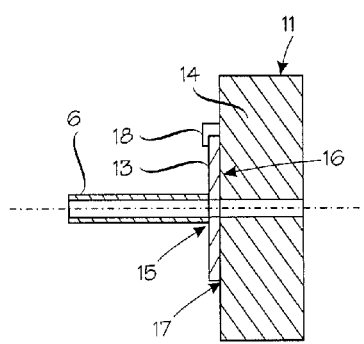
FIG. 3 schematically illustrates an examplary embodiment of the present invention.

FIG. 3 schematically illustrates an examplary embodiment of the present invention. FIG. 2 shows schematically the connection of the sampling tube 6 to the analyzer 11.

The embodiment shown comprises a first connector body 13 and a second connector body 14. The first connector body 13 comprises an element 15 for fastening the first connector body to the fluid tube 6, for example a gas sampling tube as shown in FIG. 1. The second connector body 14 is provided with mating surfaces 16, 17 to create a fluid tight seal between the first connector body 13 and the second connector body 14.

The first connector body 13 and the second connector body 14 may be separate elements so that for example the second connector body 14 may be attached to the analyzer 11. It is however also possible that said second connector body is an integral part of the analyzer 11 etc.

As described earlier there exist problems in the prior art. Said problems can however be solved with special connector geometries using special mating surfaces that significantly reduce the likelihood of generating leaking gas sample connections and virtually make those impossible. This may be accomplished with a geometry where the gas sampling line detaches from the gas detector unless it is appropriately attached and secured. The geometry offers no support for the sampling line to stay on the gas analyzer interface and does not provide a seemingly safe connection unless the mating parts are secured by using for example an appropriate locking mechanism. This can be generated by having mating parts extending into each other as little as possible before being secured and having vertical or appropriately tilted interfacing surfaces so that one connector part falls off for example because of gravity force.

The mating surfaces 16, 17 comprise only vertical and/or oblique parts and the connector structure is provided with a locking mechanism 18. The mating surfaces 16, 17 have been arranged to press tightly against each other and form a fluid tight seal with the locking mechanism 18 only. The first connector body 13 is arranged to detach from the second connector body 14 without correct use of the locking mechanism 18, i.e. if the locking mechanism 18 is not properly locked gravity force acting on the first connector body 13 in FIG. 3 forces the first connector body 13 to detach.

The embodiment described above can also be described by describing the matters in an opposite way, i.e. by describing a typical prior art design in which a narrow mating connector protrudes into a female connector and the friction between the surfaces together with gravity can generate an illusion of a secured and airtight connection.

In the embodiment of FIG. 3 the mating surfaces 16, 17 are flat surfaces. This is not however the only possibility, and the mating surfaces may have other forms too.

Figure 4:
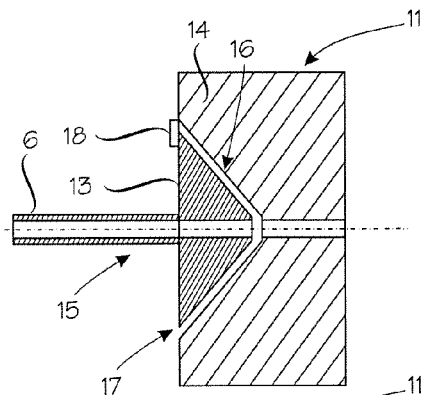
FIG. 4 schematically illustrates an examplary embodiment of the present invention.

FIG. 4 schematically illustrates an examplary embodiment of the present invention. FIG. 4 uses corresponding reference numbers as used in FIGS. 1 and 2.

In FIG. 4 the mating surfaces 16, 17 are conical surfaces. In FIG. 4 the first connector body 13 is a male part.

Figure 5:
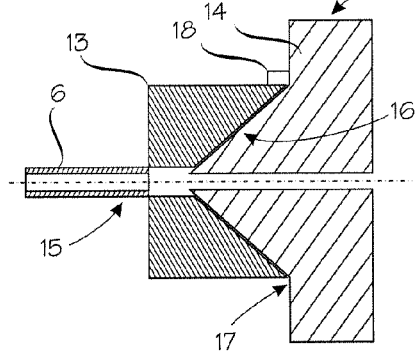
FIG. 5 schematically illustrates an examplary embodiment of the present invention.

FIG. 5 schematically illustrates an examplary embodiment of the present invention. In this embodiment the first connector part is a female part. FIG. 5 uses corresponding reference numbers as used in the previous figures.

Figure 6:
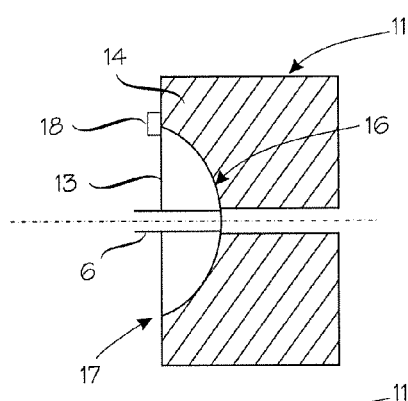
FIG. 6 schematically illustrates an examplary embodiment of the present invention.

FIG. 6 schematically illustrates an examplary embodiment of the present invention. In this embodiment the mating surfaces 16, 17 are curvilinear surfaces. FIG. 6 uses corresponding reference numbers as used in the previous figures. Also this embodiment can be materialized by forming for example the first connector body 13 as a male or a female part.

The embodiments shown in FIGS. 3-6 are structures in which the fluid line falls off from the hosting device unless deliberately secured as intended. This is achieved with mating parts that do not protrude to each other deep enough to provide support for the mating parts to stay together protruded unless the connection is deliberately secured. The mating surfaces may have small protrusive parts in order to achieve correct positioning but said protrusion is so small that it does not form any support.

In other words FIGS. 3-6 show connector structures in which the fluid line falls off from the hosting device unless deliberately secured as intended. This is achieved with mating parts that have flat, tilted or rounded mating surfaces that do not provide support for a friction based loose connection. Any incomplete interfacing would lead to the gas sampling line falling off.

Figure 7:
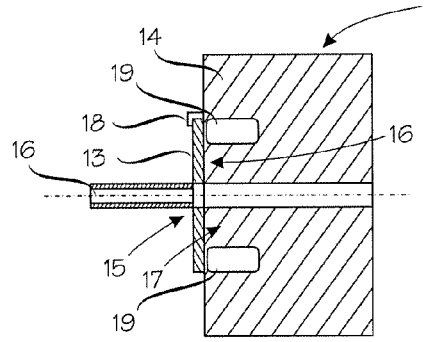
FIG. 7 schematically illustrates an examplary embodiment of the present invention.

The functionality of the fluid line falling off from the detector unless secured can be boosted further by incorporating a force between the interfaces. Said force can be created by using appropriate resilient elements 19 as shown in FIG. 7. FIG. 7 schematically illustrates an examplary embodiment of the present invention and uses corresponding reference numbers as used in the previous figures.

The resilient elements 19 may be for example spring elements.

By having the care giver deliberately work against the spring before a secure connection is made further strengthens the functionality of the designs. A spring force can be generated between the parts in several different ways. These would include (but not be limited to) having a soft compressible part between the interfaces. The compressible part could be located either on the fluid line side or on the fluid analyzer side. A spring force could also be generated by having bending pieces incorporated into the design.

Figure 8:
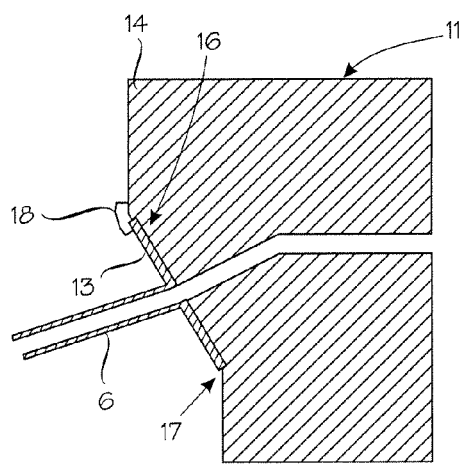
FIG. 8 schematically illustrates an examplary embodiment of the present invention.

Another means to further enhance the functionality of the connectors falling off unless secured is to make the design more susceptible to gravitation. Typically, gas sample connectors are placed on the sidewall of a monitoring device and hence the movement required for connecting the pieces happens in a horizontal plane. However, if the gas detector connector is tilted towards the ground or even positioned to point directly downwards there would be less friction to keep the pieces together than when having a horizontal connection. FIG. 8 schematically illustrates an examplary embodiment of the present invention in which the connector is tilted towards the ground as described above. FIG. 8 uses corresponding reference numbers as used in the previous figures.

The principles of the embodiments described above can be applied to several different basic connector types such as a bayonnette connector, a conical connector with a thread, groove, etc.

Figure 9:
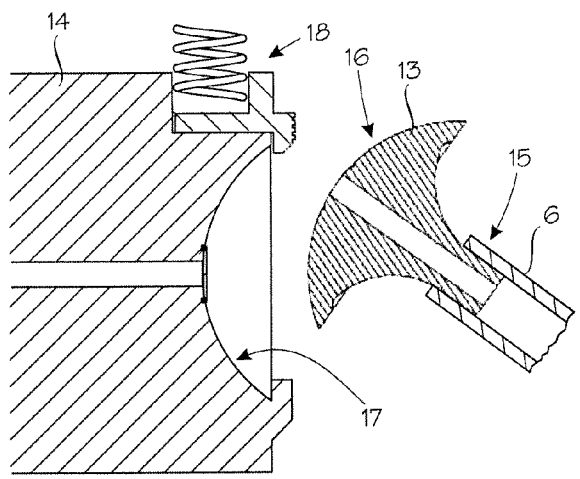
FIG. 9 schematically illustrates an examplary embodiment of the present invention in a fallen off situation.
Figure 10:
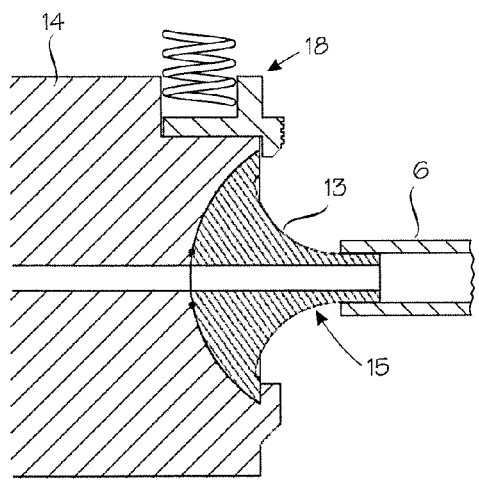
FIG. 10 schematically illustrates an examplary embodiment of the present invention in a normal operating situation.

FIGS. 9 and 10 schematically illustrate an examplary embodiment of the present invention. FIGS. 9 and 10 use corresponding reference numbers as used in the previous figures. The embodiment shown in FIGS. 9 and 10 uses the principle shown in FIG. 6, i.e. curvilinear mating surfaces 16, 17. FIGS. 9 and 10 show also that the locking mechanism 18 is a mechanism loaded by a resilient locking element. Said resilient locking element can be for example a spring element as shown in FIGS. 9 and 10 or any appropriate compressible part of resilient material.

The embodiments described above relate to the connection between the sampling tube 6 and the analyzer 11. This is not however the only possibility but the embodiments described can also be used for example as a connector structure between the sampling tube 6 and patient breathing tubing 3.

Sampling tube 6 can be provided with the first connector body 13 at one end or both ends thereof, or alternatively with the first connector body 13 at one end and the second connector body 14 at the other end. It is also quite possible that the sampling tube 6 is provided with the second connector body 14 at both ends thereof.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A connector structure for a fluid tube for connecting to a gas analyzer, the connector structure comprising:
    a locking mechanism comprising a mechanism loaded by a resilient locking element;
    a first connector body connected to a fluid tube; and
    a second connector body formed from a sidewall of a housing of the gas analyzer;
        the first connector body and the second connector body being connectable to each other and comprising mating surfaces to create a fluid tight seal between the first connector body and the second connector body, wherein the mating surfaces comprise only vertical and/or oblique parts and are configured to press tightly against each other and form the fluid tight seal with correct usage of the locking mechanism, the locking mechanism disposed on the sidewall of the housing adjacent to the second connector body; and
        the first and the second connector body are configured to fall off from each other by the effect of gravity force without correct usage of the locking mechanism.

2. The connector structure as claimed in claim 1, wherein the mating surfaces comprise flat surfaces.

3. The connector structure as claimed in claim 1, wherein the mating surfaces comprise conical surfaces.

4. The connector structure as claimed in claim 1, wherein the mating surfaces comprise curvilinear surfaces.

5. The connector structure as claimed in claim 1, wherein the mating surfaces are formed without substantially protruding components.

6. The connector structure as claimed in claim 5, wherein the mating surfaces do not provide any support for a friction based loose connection between the mating surfaces.

7. The connector structure as claimed in claim 1, wherein the connector structure further comprises resilient elements configured to boost the detaching or falling off of at least one of the first connector body and the second connector body relative to each other without correct usage of the locking mechanism.

8. The connector structure as claimed in claim 7, wherein the resilient elements comprise spring elements.

9. The connector structure as claimed in claim 1, wherein the resilient locking element comprises a spring element.

10. The connector structure as claimed in claim 1, wherein at least one of (i) the fluid tube is a sample tube of a patient respiratory gas tubing and (ii) the second connector body is a part of a gas analyzer.

11. The connector structure as claimed in claim 1, wherein the second connector body is a part of the patient respiratory tubing.

12. A connector structure of a sampling tube of a patient respiratory gas tubing for connecting to a gas analyzer, the connector structure comprising:
    a locking mechanism comprising a mechanism loaded by a resilient locking element;
    a first connector body connected to a fluid tube; and
    a second connector body;
        the first connector body and the second connector body being connectable to each other and comprising mating surfaces to create a fluid tight seal between the first connector body and the second connector body, wherein the mating surfaces comprise only vertical and/or oblique parts and are configured to press tightly against each other and form the fluid tight seal with correct usage of the locking mechanism, wherein the mating surface of the second connector body is formed from a sidewall or a bottom of a housing of the gas analyzer, and wherein the locking mechanism is disposed on the sidewall or the bottom of the housing adjacent to the second connector body; and
        the first and the second connector body are configured to fall off from each other by the effect of gravity force without correct usage of the locking mechanism.

13. The connector structure as claimed in claim 12, wherein at least one end of the sampling tube comprises the first connector body.

14. The connector structure as claimed in claim 12, wherein at least one end of the sampling tube comprises the second connector body.

15. The connector structure as claimed in claim 12, wherein the both ends of the sampling tube comprise the first connector body or the second connector body.

16. The connector structure as claimed in claim 12, wherein the mating surfaces comprise flat surfaces, conical surfaces or curvilinear surfaces.

17. The connector structure as claimed in claim 12, wherein the mating surfaces are formed without substantially protruding components.

18. The connector structure as claimed in claim 12, wherein the connector structure further comprises resilient elements configured to boost the detaching or falling off of at least one of the first connector body and the second connector body relative to each other without correct usage of the locking mechanism.

19. The connector structure as claimed in claim 12, wherein the locking mechanism comprises a mechanism loaded by a resilient locking element.

* * * * *